(12) United States Patent
Lee et al.

(10) Patent No.: US 12,174,137 B2
(45) Date of Patent: Dec. 24, 2024

(54) WELDING QUALITY INSPECTION DEVICE

(71) Applicant: LG ENERGY SOLUTION, LTD., Seoul (KR)

(72) Inventors: Jung Hoon Lee, Daejeon (KR); Su Taek Jung, Daejeon (KR); Seok Jin Kim, Daejeon (KR); Ji Hoon Lee, Daejeon (KR); Sang Hyun Koo, Daejeon (KR)

(73) Assignee: LG ENERGY SOLUTION, LTD., Seoul (KR)

( * ) Notice: Subject to any disclaimer, the term of this patent is extended or adjusted under 35 U.S.C. 154(b) by 210 days.

(21) Appl. No.: 17/769,860

(22) PCT Filed: Feb. 8, 2021

(86) PCT No.: PCT/KR2021/001653
§ 371 (c)(1),
(2) Date: Apr. 18, 2022

(87) PCT Pub. No.: WO2021/177613
PCT Pub. Date: Sep. 10, 2021

(65) Prior Publication Data
US 2022/0373493 A1    Nov. 24, 2022

(30) Foreign Application Priority Data

Mar. 2, 2020  (KR) .......................... 10-2020-0026135

(51) Int. Cl.
*G01N 27/20*    (2006.01)
*B23K 31/12*    (2006.01)
(Continued)

(52) U.S. Cl.
CPC ........... *G01N 27/20* (2013.01); *B23K 31/125* (2013.01); *G01N 27/041* (2013.01);
(Continued)

(58) Field of Classification Search
CPC ...... G01N 27/20; G01N 27/04; G01N 27/041; G01N 33/207; B23K 31/12; B23K 31/125;
(Continued)

(56) References Cited

U.S. PATENT DOCUMENTS 4,368,422 A    1/1983  Bachet et al.
7,988,745 B2   8/2011  Okabe et al.
(Continued)

FOREIGN PATENT DOCUMENTS

CN    1723389 A    1/2006
CN  103376278 A   10/2013
(Continued)

OTHER PUBLICATIONS

International Search Report (with partial translation) and Written Opinion dated May 28, 2021 issued in corresponding International Patent Application No. PCT/KR2021/001653.
(Continued)

*Primary Examiner* — Son T Le
(74) *Attorney, Agent, or Firm* — MORGAN, LEWIS & BOCKIUS LLP

(57) ABSTRACT

The present invention provides an apparatus for inspecting a welding state in a welded portion for an electronic or mechanical coupling in a lithium secondary battery, the apparatus including: a measuring unit configured to obtain data for deriving a resistance value of the welded portion by allowing a resistance measuring probe to contact the welded portion; and a controller configured to communicate with the measuring unit, determine the resistance value of the welded portion by receiving the data obtained from the measuring unit, and determine whether a weak welding was performed by comparing the determined resistance value with a threshold resistance value, in which the measuring unit is config-
(Continued)

ured to allow the resistance measuring probe to contact one end and the other end of the welded portion.

15 Claims, 8 Drawing Sheets

(51) Int. Cl.
*G01N 27/04* (2006.01)
*G01N 33/207* (2019.01)
*H01M 10/052* (2010.01)
*H01M 10/42* (2006.01)
*H01M 10/48* (2006.01)
*H01M 50/536* (2021.01)
*B23K 101/36* (2006.01)

(52) U.S. Cl.
CPC ........ *G01N 33/207* (2019.01); *H01M 10/052* (2013.01); *H01M 10/4285* (2013.01); *H01M 10/48* (2013.01); *H01M 50/536* (2021.01); *B23K 2101/36* (2018.08)

(58) Field of Classification Search
CPC ............ B23K 2101/36; H01M 10/052; H01M 10/42; H01M 10/4285; H01M 10/48; H01M 50/536; H01M 10/0525; H01M 50/531; Y02E 60/10; Y02P 70/50; G01R 27/00; G01R 27/02; G01R 27/025
See application file for complete search history.

(56) References Cited

U.S. PATENT DOCUMENTS

| | | | |
|---|---|---|---|
| 2004/0051519 A1 | 3/2004 | Cheong et al. | |
| 2010/0019785 A1 | 1/2010 | Wang et al. | |
| 2017/0322168 A1 | 11/2017 | Lupienski et al. | |
| 2019/0240788 A1 | 8/2019 | Park et al. | |
| 2021/0245292 A1* | 8/2021 | Maeda | B23K 11/11 |

FOREIGN PATENT DOCUMENTS

| | | | |
|---|---|---|---|
| CN | 109596677 A | | 4/2019 |
| CN | 109709154 A | | 5/2019 |
| CN | 109813765 A | | 5/2019 |
| CN | 110006953 A | * | 7/2019 |
| JP | S51-125974 U | | 10/1976 |
| JP | S56-94255 A | | 7/1981 |
| JP | 2000-100465 A | | 4/2000 |
| JP | 2000-268887 A | | 9/2000 |
| JP | 2004-111898 A | | 4/2004 |
| JP | 2006-200946 A | | 8/2006 |
| JP | 4330690 B2 | | 9/2009 |
| JP | 2011-100661 A | | 5/2011 |
| JP | 2013-246084 A | | 12/2013 |
| JP | 2015-225040 A | | 12/2015 |
| JP | 2019-020135 A | | 2/2019 |
| JP | 2019-56672 A | | 4/2019 |
| KR | 20-0414659 Y1 | | 4/2006 |
| KR | 10-2007-0044647 A | | 4/2007 |
| KR | 10-0902316 B1 | | 6/2009 |
| KR | 10-1058388 B1 | | 8/2011 |
| KR | 10-2013-0097990 A | | 9/2013 |
| KR | 10-2014-0141289 A | | 12/2014 |
| KR | 10-1783921 B1 | | 10/2017 |
| KR | 10-2017-0125707 A | | 11/2017 |
| KR | 10-1887148 B1 | | 8/2018 |
| KR | 10-2018-0122115 A | | 11/2018 |
| KR | 10-2057781 B1 | | 12/2019 |

OTHER PUBLICATIONS

Office action issued Oct. 10, 2023, by the Japanese Patent Office corresponding to JP Patent Application No. 2022-522697.
Extended European Search Report issued from the European Patent Office dated Aug. 30, 2022 in connection with the corresponding European Patent Application No. 21765449.0.
Office Action issued in Japanese Application 2022-522697 dated Feb. 19, 2024.
Office Action issued May 11, 2024 in Chinese Patent Application No. 202180005920.0.
Office Action dated Apr. 4, 2024, issued in Korean Patent Application No. 10-2020-0026135.

* cited by examiner

[FIG. 1]
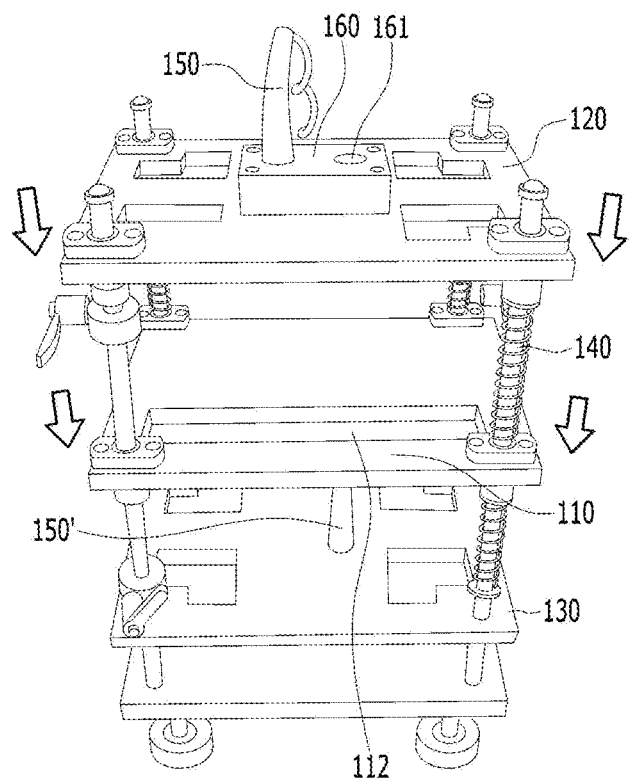

[FIG. 2]
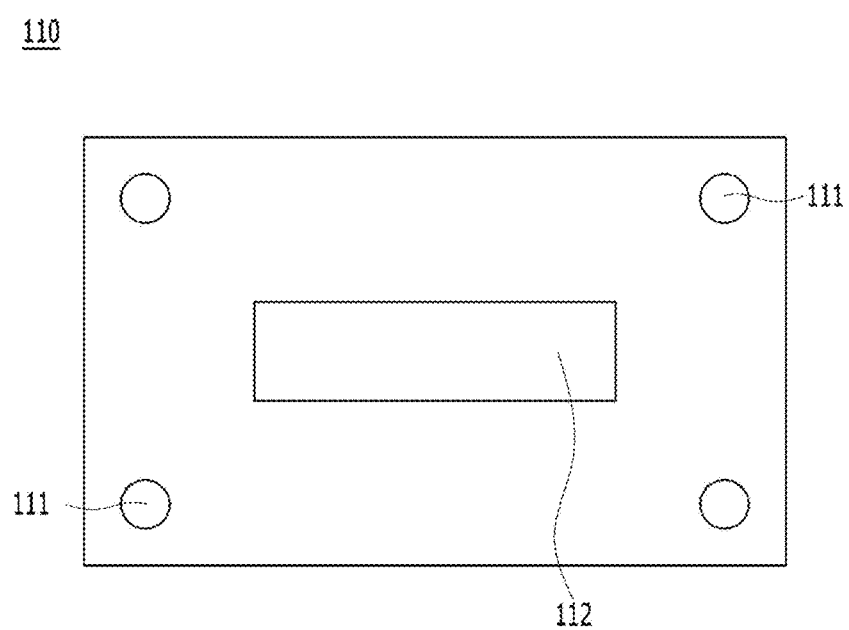

[FIG. 3]
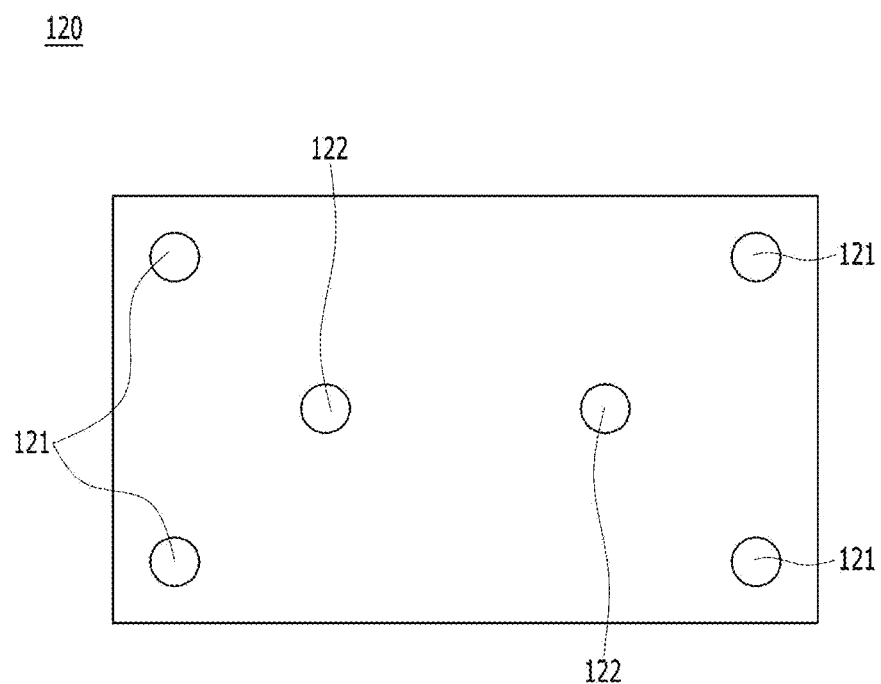

[FIG. 4]
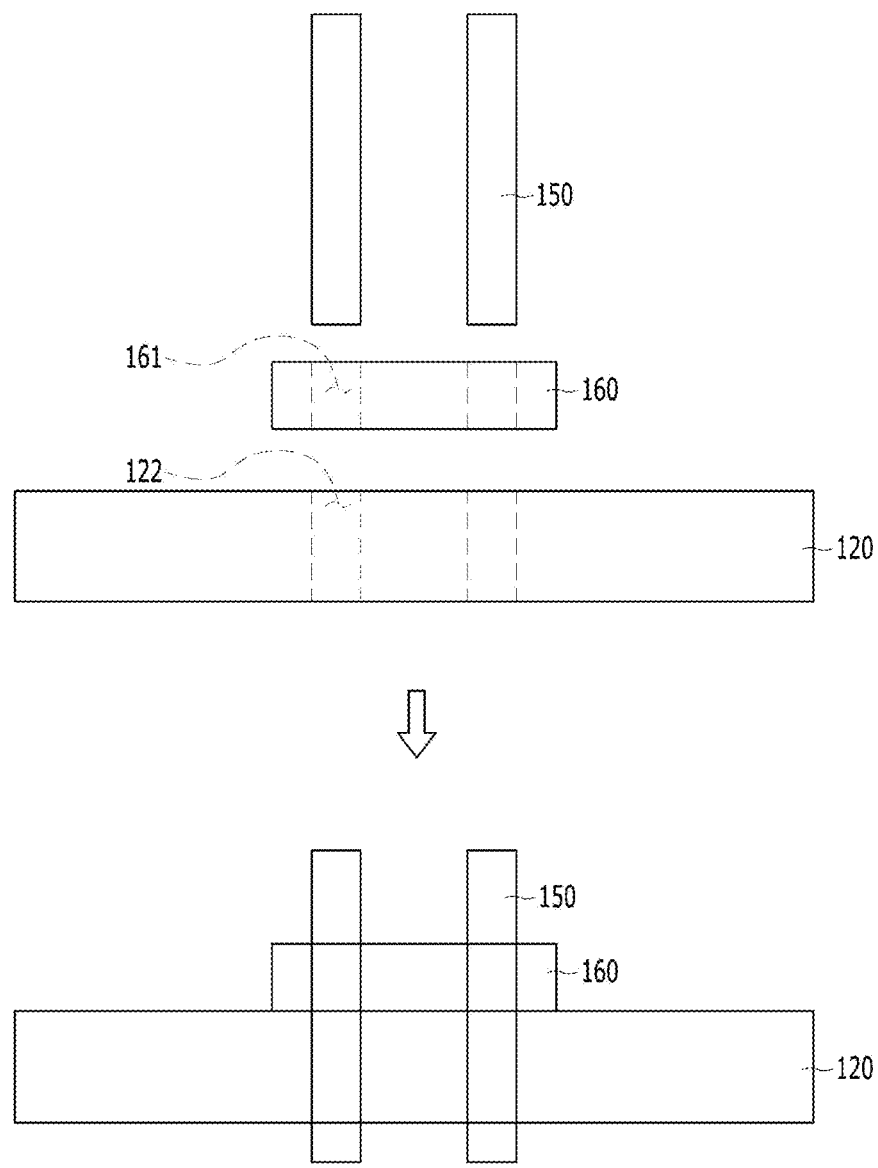

[FIG. 5]
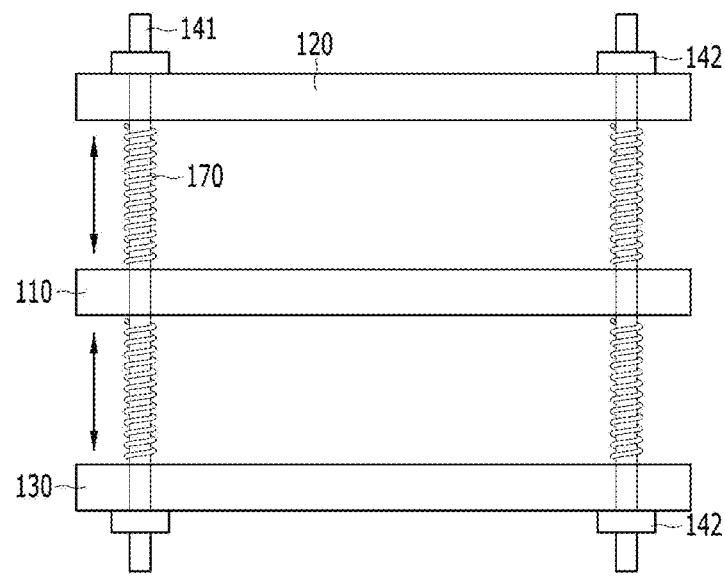
[FIG. 6]
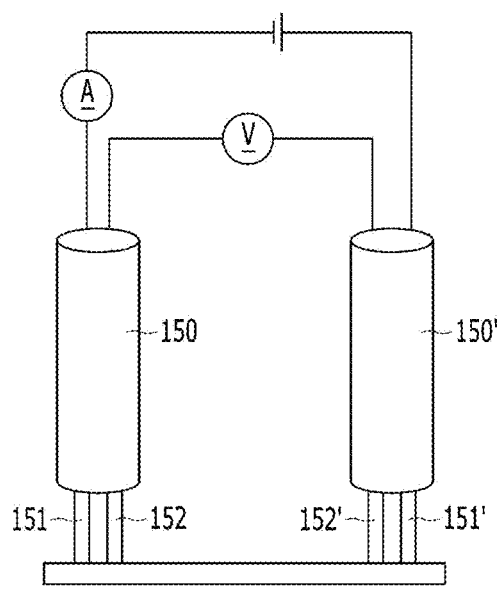

[FIG. 7]
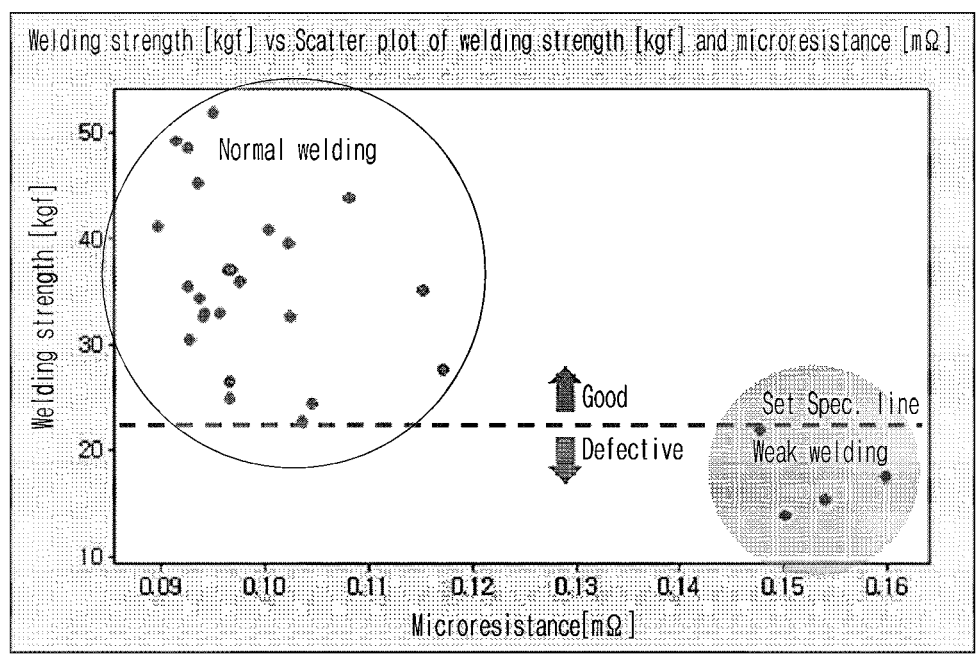

[FIG. 8]
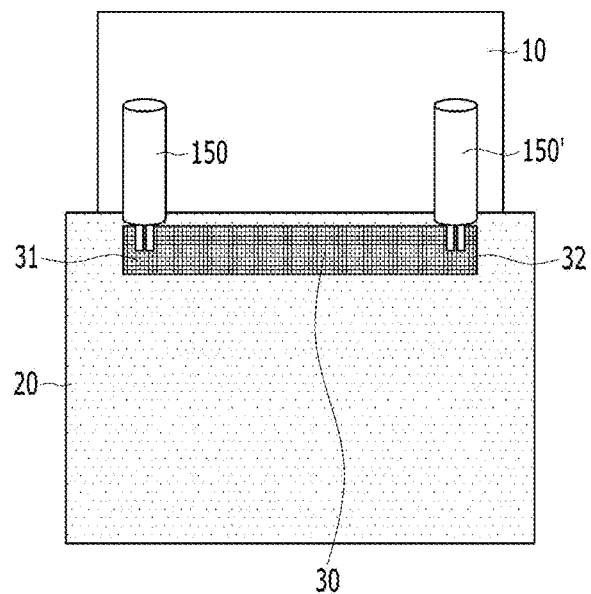
(a)
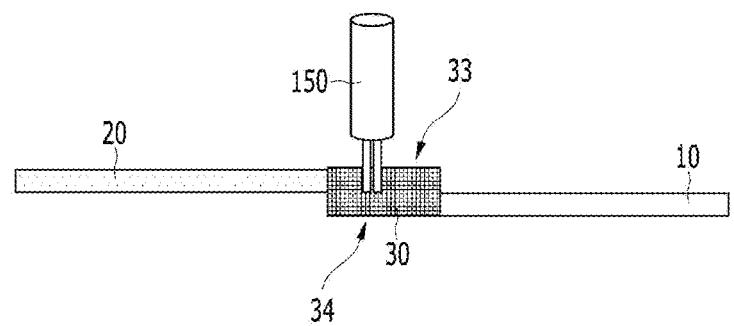
(b)

[FIG. 9]
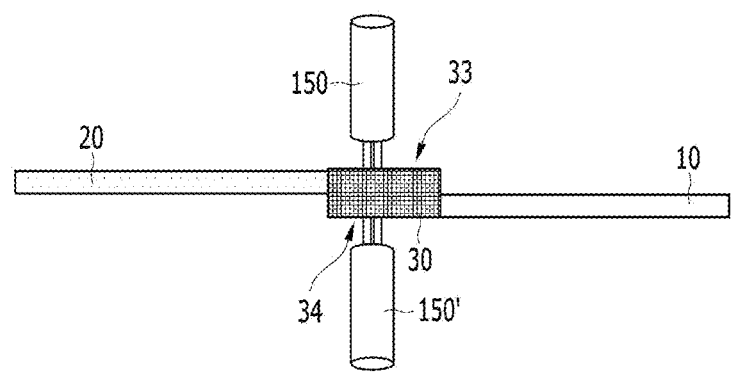
(a)
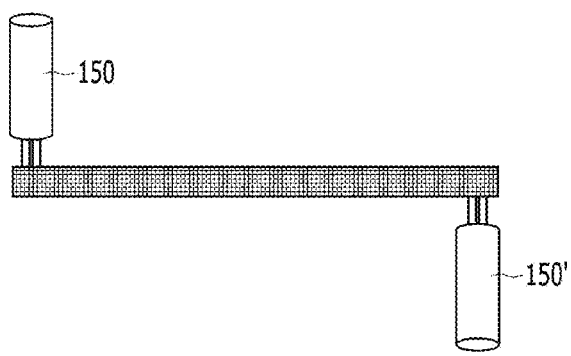
(b)

WELDING QUALITY INSPECTION DEVICE

TECHNICAL FIELD

This application claims the benefit of priority based on Korean Patent Application No. 10-2020-0026135, filed on Mar. 2, 2020, and the entire contents of the Korean patent application are incorporated herein by reference.

The present invention relates to an apparatus for inspecting a welding state in a welded portion for an electronic or mechanical coupling in a lithium secondary battery, and more particularly, to an apparatus for inspecting whether a weak welding was performed on a welded portion between an electrode tab and an electrode tab and a welded portion between an electrode tab and an electrode lead.

BACKGROUND ART

In general, a secondary battery, unlike a primary battery that cannot be charged, means a battery that can be charged and discharged, and is widely used in electronic devices such as mobile phones, notebook computers, camcorders, or electric vehicles. In particular, the lithium secondary battery has a larger capacity than a nickel-cadmium battery or a nickel-hydrogen battery, and because the energy density per unit weight is high, the degree of utilization thereof is rapidly increasing.

Further, lithium secondary batteries are classified according to the structure of the electrode assembly having a positive electrode/separator/negative electrode structure. Representative examples thereof include a jelly-roll electrode assembly in which long sheet type positive electrodes and negative electrodes are wound with a separator interposed therebetween, a stacked electrode assembly in which a plurality of positive and negative electrodes cut in a predetermined size unit are sequentially stacked with a separator interposed therebetween, and a stacked/foldable electrode assembly in which bi-cells or full cells, in which positive and negative electrodes of a predetermined unit are stacked with a separator interposed therebetween, are wound.

In recent years, a pouch type battery having a stack type or stack/folding type electrode assembly embedded in a pouch-shaped battery case of an aluminum laminate sheet has attracted a lot of attention due to its low manufacturing cost and small weight, and the amount used thereof is gradually increasing.

The lithium secondary battery mainly uses a lithium-based oxide and a carbon material as a positive electrode active material and a negative electrode active material, respectively. The lithium secondary battery includes an electrode assembly, in which a positive electrode plate and a negative electrode plate coated with the positive electrode active material and the negative electrode active material, respectively, are disposed with a separator therebetween, and an exterior material that seals and stores the electrode assembly together with the electrolyte.

At this time, a plurality of positive electrode tabs, which are extended from a plurality of positive electrode plates, and a plurality of negative electrode tabs, which are extended from a plurality of negative electrode plates, are formed in the electrode assembly, and the plurality of positive electrode tabs and the plurality of negative electrode tabs are respectively coupled with the positive electrode lead and the negative electrode lead by welding. Herein, a plurality of positive electrode tabs and a plurality of negative electrode tabs form an electrode tab, and a positive electrode lead and a negative electrode lead form an electrode lead.

Likewise, when the electrode tab and the electrode lead are welded, if a weak welding is performed between the electrode tabs and between the electrode tab and the electrode lead, a welding defect may be generated. Hence, there is a need for a process of inspecting whether there is a welding defect by such a weak welding.

Conventionally, in order to inspect a welding defect by a weak welding on the welded portion, tensile strength was measured by pulling the welded portion in an opposite direction. However, when using such a method, the electrode tab or the electrode lead may be damaged in the process of measuring the tensile strength. Hence, complete enumeration was not possible. Therefore, there is a need for a technology about an apparatus for inspecting a weak welding of a welded portion with excellent detection power while allowing complete enumeration.

DISCLOSURE

Technical Problem

As such, the present invention was devised to solve the above problems, and an object of the present invention is to provide an apparatus for inspecting a weak welding of a welded portion with excellent detection power while allowing complete enumeration.

Technical Solution

A welding state inspection apparatus of the present invention for achieving the above purposes is an apparatus for inspecting a welding state in a welded portion for an electronic or mechanical coupling in a lithium secondary battery, the apparatus including: a measuring unit configured to obtain data for deriving a resistance value of the welded portion by allowing a resistance measuring probe to contact the welded portion; and a controller configured to communicate with the measuring unit, determine the resistance value of the welded portion by receiving the data obtained from the measuring unit, and determine whether a weak welding was performed by comparing the determined resistance value with a threshold resistance value, wherein the measuring unit is configured to allow the resistance measuring probe to contact one end and the other end of the welded portion.

In one specific example, the controller determines that a weak welding was performed if the determined resistance value exceeds the threshold resistance value.

In one specific example, the measuring unit includes: a flat cradle on which a subject is mounted; an upper plate configured to be positioned on an upper portion having a predetermined separation distance from the cradle and include a plurality of through holes into which the resistance measuring probe is insertable; a lower plate configured to be positioned on a lower portion having a predetermined separation distance from the cradle and include a plurality of through holes into which the resistance measuring probe is insertable; a coupling unit configured to allow the cradle, the upper plate and the lower plate to be coupled to each other; and a pair of resistance measuring probes configured to obtain data for determining a resistance value by contacting the welded portion.

In one specific example, one resistance measuring probe includes a current probe and a voltage probe.

In one specific example, an upper guide member and a lower guide member for allowing the resistance measuring probe to be inserted into a correct position are coupled to the upper plate and the lower plate, respectively.

In one specific example, the upper guide member and the lower guide member have through holes into which the resistance measuring probe is insertable, respectively, the through holes of the upper guide member and the through holes of the upper plate are located on a straight line to thereby allow the resistance measuring probe to pass the through holes to approach an upper surface of the welded portion, and the through holes of the lower guide member and the through holes of the lower plate are located on a straight line to thereby allow the resistance measuring probe to pass the through holes to approach a lower surface of the welded portion.

In one specific example, the coupling unit includes a coupling bar and a coupling screw. In one specific example, the cradle, the upper plate and the lower plate each has coupling holes at 4 edge portions, and the upper plate, the cradle and the lower plate are coupled as the coupling bar sequentially passes through coupling holes formed on the upper plate, the cradle and the lower plate.

In one specific example, the apparatus further includes a compression spring for adjusting a separation distance between the cradle and the upper plate and a separation distance between the cradle and the lower plate, wherein the coupling bar is configured to be insertable into a hollow portion of the compression spring.

In one specific example, the controller includes a threshold resistance value setting program for setting the threshold resistance value by processing data obtained for a sample group by a statistical scheme.

In one specific example, resistance values determined from data obtained for the sample group form a normal distribution curve.

In one specific example, the inspection apparatus of the present invention further includes an output unit configured to display data obtained from the measuring unit and resistance values of the welded portion determined by the controller.

In one specific example, the inspection apparatus of the present invention further includes a power source configured to apply power to the measuring unit, wherein the power is a direct current (DC) power and is controlled by the controller.

Advantageous Effects

According to the welded state inspection method of the present invention, resistances of a sample group are measured, a threshold resistance value is set from a normal distribution curve of the measured resistance values, and microresistances having a resolution of nanoohm to microohm levels can be measured when measuring resistances for the sample group and the welded portion to be inspected, thereby showing an excellent detection power for a weak welding defect.

BRIEF DESCRIPTION OF THE DRAWINGS

FIG. 1 is a schematic diagram of a measuring unit constituting the welding state inspection apparatus of the present invention.

FIG. 2 is a plan view of a cradle constituting the measuring unit of FIG. 1.

FIG. 3 is a plan view of an upper plate constituting the measuring unit of FIG. 1.

FIG. 4 is a coupling diagram of an upper plate and an upper guide member according to an embodiment of the present invention.

FIG. 5 is a front view of FIG. 1.

FIG. 6 is a schematic diagram of a resistance measuring probe according to an embodiment of the present invention.

FIG. 7 is a graph showing the correlation between welding strength and resistance.

FIG. 8 is a schematic diagram showing a method of measuring a resistance according to an embodiment of the present invention.

FIG. 9 is a schematic diagram showing a method of measuring a resistance according to another embodiment of the present invention.

DETAILED DESCRIPTION OF THE PREFERRED EMBODIMENTS

Hereinafter, preferred embodiments of the present invention will be described in detail with reference to the accompanying drawings. The terms and words used in the present specification and claims should not be construed as limited to ordinary or dictionary terms and the inventor may properly define the concept of the terms in order to best describe its invention. The terms and words should be construed as meaning and concept consistent with the technical idea of the present invention.

Accordingly, the embodiments described in the specification and the configurations described in the drawings are only the most preferred embodiments of the present invention, and do not represent all of the technical ideas of the present invention. It is to be understood that there may be various equivalents and variations in place of them at the time of filing the present application.

Also, throughout the specification, when an element is referred to as "including" an element, it is understood that the element may include other elements as well unless specifically stated otherwise.

The present invention provides an apparatus for inspecting a welding state in a welded portion for an electronic or mechanical coupling in a lithium secondary battery, the apparatus including: a measuring unit configured to obtain data for deriving a resistance value of the welded portion by allowing a resistance measuring probe to contact the welded portion; and a controller configured to communicate with the measuring unit, determine the resistance value of the welded portion by receiving the data obtained from the measuring unit, and determine whether a weak welding was performed by comparing the determined resistance value with a threshold resistance value, in which the measuring unit is configured to allow the resistance measuring probe to contact one end and the other end of the welded portion.

FIG. 6 is a schematic diagram of a resistance measuring probe according to an embodiment of the present invention. Referring to FIG. 6, a pair of resistance measuring probes 150 and 150' of the present invention are provided, which include a pair of current probes and a pair of voltage probes. Namely, one resistance measuring probe 150 includes a current probe 151 and a voltage probe 152, and another resistance measuring probe 150' also includes a current probe 151' and a voltage probe 152'. As such, the resistance of the welded portion can be measured by a 4-wire type measuring scheme. The current probe applies current to a welded portion to be measured, and the voltage probe measures voltages. As such, the resistance of the welded portion can be determined.

In the present invention, data for determining the resistance value is obtained by allowing a pair of resistance measuring probes to contact the welded portion. As such, the resistance of the welded portion can be measured by a 4-wire type measuring scheme. Since the 4-wire type resistance measuring scheme is less influenced by the contact resistance compared to the 2-wire type resistance measuring scheme, the microresistance can be more precisely measured in the 4-wire type resistance measuring scheme, in which the resistance can be measured even in nanoohm units.

FIG. 1 is a schematic diagram of a measuring unit 100 constituting the welding state inspection apparatus according to an embodiment of the present invention. Referring to FIG. 1, the measuring unit 100 of the present invention includes: a flat cradle 110 on which a subject is mounted; an upper plate 120 configured to be positioned on an upper portion having a predetermined separation distance from the cradle and include a plurality of through holes into which the resistance measuring probe is insertable; a lower plate 130 configured to be positioned on a lower portion having a predetermined separation distance from the cradle and include a plurality of through holes into which the resistance measuring probe is insertable; a coupling unit 140 configured to allow the cradle, the upper plate and the lower plate to be coupled to each other; and a pair of resistance measuring probes 150 and 150' configured to obtain data for determining a resistance value by contacting the welded portion.

The cradle 110 is a flat rectangular member on which a subject including a welded portion to be inspected is placed, and the subject is mounted on the central portion. FIG. 2 is a plan view of a cradle 110 according to an embodiment of the present invention. Referring to FIG. 2, the cradle 110 of the present invention includes a plurality of coupling holes 111 into which the coupling bar to be described later can be inserted, and the coupling holes are formed at 4 edge portions of the cradle. Further, a rectangular through hole 112 is formed on a portion corresponding to the welded portion of the subject in a thickness direction of the cradle to allow the resistance measuring probe to contact the top and backside of the welded portion, and the welded portion is positioned in the through hole 112 region.

The upper plate 120 is positioned at a point having a predetermined separation distance in a vertical upper direction from the cradle 110. The upper plate is flat like the cradle and includes a plurality of through holes into which the resistance measuring probe including a current probe and a voltage probe can be inserted. FIG. 3 is a plan view of the upper plate 120 according to one embodiment. Referring to FIG. 3, the upper plate of the present invention is a flat rectangular member and has coupling holes 121 at 4 edge portions, respectively. Further, the coupling bars (not shown) to be described later are inserted into the coupling holes. The upper plate 120 includes through holes 122 into which the resistance measuring probe can be inserted. A plurality of through holes are formed at portions corresponding to one end and the other end of the welded portion. As such, the resistance measuring probe can approach one end and the other end of the welded portion. Further, the resistance measuring probe, which is inserted into the upper plate, can approach the top of the welded portion.

The lower plate 130 is positioned at a point having a predetermined separation distance in a vertical lower direction from the cradle 110. The lower plate is a flat rectangular member and has a plurality of through holes in which the resistance measuring probe can be inserted like the upper plate. 4 edge portions of the lower plate have coupling holes, respectively, and the coupling bars to be described later are inserted into the coupling holes. The lower plate has a plurality of through holes, into which the resistance measuring probe can be inserted, as in the upper plate, and the through holes may be formed on portions corresponding to one end and the other end of the welded portions. As such, the resistance measuring probe can approach one end and the other end of the welded portion. Further, the resistance measuring probe, which is inserted into the lower plate, can approach the backside of the welded portion.

Likewise, as the upper plate and the lower plate include a plurality of through holes into which the resistance measuring probe can be inserted, the inserted location of the resistance measuring probe can be appropriately adjusted according to the inspected location of the welded portion.

Referring to FIG. 1, the upper guide member 160 and the lower guide member (not shown) are coupled with the upper plate 120 and the lower surface 130, respectively. The upper guide member 160 and the lower guide member (not shown) allow the resistance measuring probe to be inserted at a correct position.

Hereinafter, the upper guide member will be described. FIG. 4 is a coupling diagram of an upper plate and an upper guide member according to an embodiment of the present invention. Referring to FIG. 4, the upper guide member 160 includes a plurality of through holes 161 into which the resistance measuring probe can be inserted. According to the embodiment illustrated in FIG. 4, there are two through holes, and the resistance measuring probe can be inserted into each of the through holes. The through holes are formed on portions corresponding to one end and the other end of the welded portion. The resistance measuring probe can be inserted into both one end and the other end of the welded portion, or the resistance measuring probe can also be inserted into only one of one end and the other end of the welded portion.

Further, the upper plate 120 has a plurality of through holes 122. The resistance measuring probe 150 sequentially passes through the through hole 161 of the upper guide member 160 and the through holes 122 of the upper plate 120, to thereby approach the upper surface of the welded portion of the subject. At this time, in order to allow the resistance measuring probe to pass through all of the through hole 161 of the upper guide member and the through hole 122 of the upper plate, the through holes are placed on a straight line in a direction in which the resistance measuring probe is inserted as in FIG. 4. As such, the upper guide member 160 allows the resistance measuring probe to be inserted in the thickness direction of the upper plate in a non-inclined state and fixes the resistance measuring probe.

Though not illustrated in FIG. 4, the lower guide member is coupled with the lower plate, and the lower guide member includes a plurality of through holes into which the resistance measuring probe can be inserted, as in the upper guide member. Further, there may be two through holes, and the resistance measuring probe may be inserted into each of the through holes. The lower plate includes through holes as in the upper plate, and the resistance measuring probe sequentially the through hole of the lower guide member and the through hole of the lower plate, to thereby approach the lower surface of the welded portion of the subject on the cradle. At this time, in order to allow the resistance measuring probe to pass through all of the through hole of the lower guide member and the through hole of the lower plate, the through hole of the lower guide member and its corresponding through hole of the lower plate are placed on a straight line in a direction in which the resistance measuring probe is inserted. Such a lower guide member fixes the resistance measuring probe while allowing the resistance measuring probe to be inserted in a non-inclined manner as in the upper guide member.

The cradle, the upper plate and the lower plate constituting the measuring unit of the present invention are coupled by the coupling unit. As described above, the cradle, the upper plate and the lower plate include coupling holes at 4 edge portions, and the coupling unit includes a coupling bar and coupling screws.

Referring to FIGS. 1 to 5, the coupling unit 140 of the present invention is configured to allow the coupling bar 141 to pass through the coupling holes of the upper plate 120, the cradle 110 and the lower plate 130 to be inserted, to thereby allow the upper plate, the cradle and the lower plate to be coupled with each other.

Further, the measuring unit 100 of the present invention further includes a compression spring 170 for adjusting a separation distance between the cradle 110 and the upper plate 120 and a separation distance between the cradle 110 and the lower plate 130, and the coupling bar 141 can be inserted into the hollow portion of the compression spring 170. The upper plate 120 and the lower plate 130 may respectively move along the coupling bar 141 in a vertical direction by elasticity of the compression spring 170. By applying a load to the upper plate 120 and/or the lower plate 130 in the direction of the cradle 110, the upper plate 120 and/or the lower plate 130 may be positioned at desired positions and they may then fixed at desired positions by using coupling screws 142. Further, the compression spring 170 may have a length of a distance from the upper plate to the lower plate corresponding to one coupling bar 141, but one coupling bar 141 may pass through two compression springs. In this case, one compression spring has a length corresponding to the length between the upper plate 120 and the cradle 110, and another compression spring has a length corresponding to the length between the lower plate 130 and the cradle 110.

In one specific example, the welding state inspection apparatus of the present invention further includes an output unit configured to display data obtained from the measuring unit and resistance values of the welded portion determined by the controller. The inspection performer can check the resistance value of the welded portion to be inspected through the output unit.

In one specific example, the welding state inspection apparatus of the present invention further includes a power source for applying power to the measuring unit. The power is preferably DC power. This is because the direct current scheme has an advantage that high-precision resistance measurement is possible, compared to the alternating current scheme. The controller controls the size of the current applied to the measuring unit, the current application time, and the point of time of applying the current, etc.

The controller of the present invention will be described in detail.

The controller of the present invention communicates with the measuring unit, determines the resistance value of the welded portion by receiving the data obtained from the measuring unit, and determines whether a weak welding was performed by comparing the determined resistance value with a threshold resistance value.

In the inspection apparatus of the present invention, the controller includes a threshold resistance value setting program for setting the threshold resistance value by processing data obtained for a sample group by a statistical scheme.

The inventors of the present invention have found that the electric resistance value of the welded portion having a low welding strength was greater than the electric resistance value of the welded portion having a normal welding strength, which has led them to the present invention. Referring to FIG. 7, a resistance value of a welded portion having been welded by a normal welding strength of 22 kgf or more is smaller than a resistance value of a welded portion having been welded by a weak welding strength less than 22 kgf. Conventionally, there was a technology of inspecting a welding defect by measuring the resistance of the welded portion and comparing the measured resistance value with the threshold resistance value. However, in the conventional technology, a separate process of measuring the tensile strength of the welded portion was necessary because the correlation between the tensile strength of the welded portion and the resistance was used when deriving the threshold resistance value.

However, the inspection apparatus of the present invention does not rely on the correlation between the resistance and the tensile strength of the welded portion and uses a statistical scheme in deriving a threshold resistance value, and precisely measures the resistance by measuring the resistance up to nanoohm to microohm units by increasing the resolution in obtaining data for determining the resistance value of the welded portion.

Generally, resistance values form a normal distribution curve from data obtained for a large amount of sample groups. In the normal distribution curve, an object having a large deviation may be easily assumed as being defective from a standpoint of a statistical probability, and thus a predetermined deviation is determined as a threshold resistance value. Further, this approach is based on a premise that data for the sample group are reliable. Hence, a measuring unit of the present invention capable of precisely measuring the resistance up to nanoohm to microohm levels for the sample group is used in the process of setting a threshold value, and a measuring unit of the present invention capable of precisely measuring the resistance up to nanoohm to microresistance levels is used when measuring the resistance for the object to be inspected. Likewise, the controller constituting the inspection apparatus of the present invention includes a program for setting a threshold resistance value by processing data obtained by the measuring unit for a sample group by a statistical scheme. As such, there is no need for separately measuring the tensile strength of the welded portion in order to set the threshold resistance value unlike the conventional technology.

The welding defect inspection method using the inspection apparatus of the present invention will be described in detail. A method for inspecting a welding defect according to an embodiment of the present invention includes: a threshold resistance setting step (S100) of measuring a resistance of a welded portion of a sample group and deriving a threshold resistance value which becomes an evaluation standard of a weak welding; a resistance measuring step (S200) of measuring a resistance value of a welded portion to be inspected; and a step (S300) of determining as a weak welding if the resistance value measured in the resistance measuring step exceeds the threshold resistance value, wherein the threshold resistance setting step (S100) and the resistance measuring step (S200) include using the above-described measuring unit.

First, the threshold resistance setting step (S100) will be described.

The threshold resistance setting step (S100) includes: a data construction step (S110) for determining the resistance value of a welded portion of a sample group and storing the determined resistance value; and a threshold resistance value deriving step (S120) for deriving the threshold resistance value by processing data accumulated by the data construction step (S110) by a statistical scheme.

The data construction step (S110) includes the process of obtaining data for determining the resistance of the welded portion for a large amount of objects constituting a sample group by using the measuring unit constituting the inspection apparatus of the present invention, and determining the resistance value based on the obtained data. A pair of resistance measuring probes constituting the measuring unit of the present invention are allowed to contact the welded portion. At this time, since one resistance measuring probe includes a current probe and a voltage probe, a pair of resistance measuring probes include a pair of current probes and a pair of voltage probes. As such, 4-wire type resistance measurement is possible. The 4-wire type resistance measuring scheme has an advantage of being capable of more precisely obtaining data due to a small contact resistance, compared to the 2-wire type resistance measuring scheme.

In the data construction step (S110), the number of objects of the sample group is at least 100,000, preferably 200,000, and it is preferable to have as many objects of the sample group as possible in terms of reliability.

The threshold resistance value deriving step (S120) includes deriving a threshold resistance value by processing data accumulated by the data construction step (S110) by a statistical scheme. The controller constituting the inspection apparatus of the present invention includes a program for setting a threshold resistance value by processing data by a statistical scheme. In one specific example, the program may obtain a normal distribution curve of individual resistance values held by objects of the sample group, and in the normal distribution curve, +6σ value may be set as the threshold resistance value.

When the sample group shows a normal distribution curve, most of objects come to have a value close to the average value (u), and only a small amount of objects are significantly deviated from the average value (u). Therefore, objects having a value, which is significantly deviated from the average value, may be stochastically assumed as being defective. Specifically, the probability that an object having a deviation of 1σ (standard deviation) appears is about 32%, the probability that an object having a deviation of 2σ appears is about 5%, the probability that an object having a deviation of 3σ appears is about 0.3%, the probability that an object having a deviation of 4σ appears is about 0.01%, the probability that an object having a deviation of 5σ appears is about 0.001%, and the probability that an object having a deviation of 6σ appears is about 0.0000001%. Therefore, even if the sum of the average value and 6σ is set as the threshold resistance value and it is assumed the resistance value greater than the sum indicates that a weak welding has been performed, the reliability is very high.

Hereinafter, the resistance measuring step (S200) will be described in detail. The resistance measuring step (S200) includes obtaining data for determining the resistance value of the welded portion to be inspected by the measuring unit constituting the inspection apparatus of the present invention.

The measuring unit of the present invention includes two resistance measuring probes and obtains data for deriving the resistance value by allowing the two resistance measuring probes to contact the welded portion. FIG. 8 is a schematic diagram showing a process of acquiring data using a resistance measuring probe according to one embodiment of the present invention. Referring to FIG. 8, one resistance measuring probe 150 is allowed to contact one end 31 of the welded portion 30, and the remaining one resistance measuring probe 150' is allowed to contact the other end 32 of the welded portion 30, to thereby measure the entire resistance of the welded portion 30. Further, according to the embodiment of FIG. 8, two resistance measuring probes 150 and 150' are positioned on the upper surface of the welded portion. As illustrated in FIG. 8, the welded portion 30 can be divided into a welded portion 33 of the electrode tab 20 portion and a welded portion 34 of the electrode lead 10, and both of the two resistance measuring probes can be allowed to contact the welded portion 33 of the electrode tab. Alternatively, all of the two resistance measuring probes can be allowed to contact the welded portion 34 of the electrode lead portion.

FIG. 9 is a schematic diagram showing a process of acquiring data using a resistance measuring probe according to another embodiment of the present invention. Referring to FIG. 9, one resistance measuring probe 150 may be allowed to contact the welded portion 33 of the electrode tab portion, and the remaining one resistance measuring probe 150' may be allowed to contact the welded portion of the electrode lead portion, to thereby perform resistance measurement. Among the above embodiments, it was most preferable to measure the resistance in the form of contacting both of the two resistance measuring probes on the welded portion 33 of the electrode tab part in terms of the detection power of detecting a weak welding.

The welding state inspection apparatus and welding defect inspection method of the present invention can be widely applied to the welded portion of the secondary battery and can be applied to the welded portion according to various welding schemes. Namely, the welding defect inspection method of the present invention can be applied to a welded portion between an electrode tab and an electrode tab, a welded portion between an electrode tab and an electrode lead, and a welded portion between an electrode lead and a bus bar in a battery pack, and may also be applied to a welded portion by ultrasonic welding and a welded portion by laser welding, etc.

According to the welding state inspection apparatus of the present invention, resistances of a sample group are measured, a threshold resistance value is set from a normal distribution curve of the measured resistance values, and resistances are precisely measured by using a microresistance measuring instrument having a resolution of nanoohm to microohm levels when measuring resistances for the sample group and the welded portion to be inspected, thereby showing an excellent detection power for a weak welding defect.

The invention claimed is:

1. An apparatus for inspecting a welding state in a welded portion for an electronic or mechanical coupling in a lithium secondary battery, comprising:
a measuring unit configured to obtain data for deriving a resistance value of the welded portion by allowing a resistance measuring probe to contact the welded portion; and
a controller configured to communicate with the measuring unit, determine the resistance value of the welded portion by receiving the data obtained from the measuring unit, and determine whether a weak welding was performed by comparing the determined resistance value with a threshold resistance value, wherein the measuring unit comprises:
a pair of resistance measuring probes configured to obtain data for determining the resistance value by contacting one end and the other end of the welded portion;
a flat cradle on which a subject is mounted;
an upper plate on an upper portion having a predetermined separation distance from the flat cradle and includes a plurality of through holes into which the resistance measuring probe is insertable;
a lower plate on a lower portion having a predetermined separation distance from the flat cradle and includes a plurality of through holes into which the resistance measuring probe is insertable; and
a coupling unit configured to allow the flat cradle, the upper plate and the lower plate to be coupled to each other, and including a coupling bar and a coupling screw,
wherein each of the pair of resistance measuring probes comprises a current probe and a voltage probe, and
wherein the resistance value of the welded portion is measured by a 4-wire measuring scheme,
wherein the flat cradle, the upper plate and the lower plate each has coupling holes at 4 edge portions, and
wherein the flat cradle, the upper plate and the lower plate are coupled as the coupling bar sequentially passes through coupling holes disposed on the upper plate, the flat cradle and the lower plate.

2. The apparatus of claim 1, wherein the controller determines that a weak welding was performed if the determined resistance value exceeds the threshold resistance value.

3. The apparatus of claim 1, wherein an upper guide member and a lower guide member for allowing the resistance measuring probe to be inserted into a correct position are coupled to the upper plate and the lower plate, respectively.

4. The apparatus of claim 3, wherein the upper guide member and the lower guide member have through holes into which the resistance measuring probe is insertable, respectively,
wherein the through holes of the upper guide member and the through holes of the upper plate are located on a straight line to thereby allow the resistance measuring probe to pass the through holes to approach an upper surface of the welded portion, and
wherein the through holes of the lower guide member and the through holes of the lower plate are located on a straight line to thereby allow the resistance measuring probe to pass the through holes to approach a lower surface of the welded portion.

5. The apparatus of claim 1, wherein the controller includes a threshold resistance value setting program for setting the threshold resistance value by processing data obtained for a sample group by a statistical scheme.

6. The apparatus of claim 5, wherein resistance values determined from data obtained for the sample group correspond to a normal distribution curve.

7. The apparatus of claim 1, further comprising a power source configured to apply power to the measuring unit,
wherein the power is a direct current (DC) power and is controlled by the controller.

8. An apparatus for inspecting a welding state in a welded portion for an electronic or mechanical coupling in a lithium secondary battery, comprising:
a measuring unit configured to obtain data for deriving a resistance value of the welded portion by allowing a resistance measuring probe to contact the welded portion; and
a controller configured to communicate with the measuring unit, determine the resistance value of the welded portion by receiving the data obtained from the measuring unit, and determine whether a weak welding was performed by comparing the determined resistance value with a threshold resistance value,
wherein the measuring unit comprises:
a pair of resistance measuring probes configured to obtain data for determining the resistance value by contacting one end and the other end of the welded portion;
a flat cradle on which a subject is mounted;
an upper plate on an upper portion having a predetermined separation distance from the flat cradle and includes a plurality of through holes into which the resistance measuring probe is insertable;
a lower plate on a lower portion having a predetermined separation distance from the flat cradle and includes a plurality of through holes into which the resistance measuring probe is insertable; and
a coupling unit configured to allow the flat cradle, the upper plate and the lower plate to be coupled to each other, and including a coupling bar and a coupling screw,
wherein each of the pair of resistance measuring probes comprises a current probe and a voltage probe, and
wherein the apparatus further comprises a compression spring for adjusting a separation distance between the flat cradle and the upper plate and a separation distance between the flat cradle and the lower plate,
wherein the resistance value of the welded portion is measured by a 4-wire measuring scheme,
wherein the coupling bar is configured to be insertable into a hollow portion of the compression spring.

9. The apparatus of claim 8, wherein the controller determines that a weak welding was performed if the determined resistance value exceeds the threshold resistance value.

10. The apparatus of claim 8, wherein an upper guide member and a lower guide member for allowing the resistance measuring probe to be inserted into a correct position are coupled to the upper plate and the lower plate, respectively.

11. The apparatus of claim 10, wherein the upper guide member and the lower guide member have through holes into which the resistance measuring probe is insertable, respectively,
wherein the through holes of the upper guide member and the through holes of the upper plate are located on a straight line to thereby allow the resistance measuring probe to pass the through holes to approach an upper surface of the welded portion, and
wherein the through holes of the lower guide member and the through holes of the lower plate are located on a straight line to thereby allow the resistance measuring probe to pass the through holes to approach a lower surface of the welded portion.

12. The apparatus of claim 8, wherein the controller includes a threshold resistance value setting program for setting the threshold resistance value by processing data obtained for a sample group by a statistical scheme.

13. The apparatus of claim 12, wherein resistance values determined from data obtained for the sample group correspond to a normal distribution curve.

14. The apparatus of claim 8, further comprising a power source configured to apply power to the measuring unit,
wherein the power is a direct current (DC) power and is controlled by the controller.

15. An apparatus for inspecting a welding state in a welded portion for an electronic or mechanical coupling in a lithium secondary battery, comprising:
a measuring unit configured to obtain data for deriving a resistance value of the welded portion by allowing a resistance measuring probe to contact the welded portion; and
a controller configured to communicate with the measuring unit, determine the resistance value of the welded portion by receiving the data obtained from the measuring unit, and determine whether a weak welding was performed by comparing the determined resistance value with a threshold resistance value,
wherein the measuring unit is configured to allow the resistance measuring probe to contact one end and the other end of the welded portion,
wherein the measuring unit comprises:
a flat cradle on which a subject is mounted;
an upper plate configured to be positioned on an upper portion having a predetermined separation distance from the flat cradle and includes a plurality of through holes into which the resistance measuring probe is insertable;
a lower plate configured to be positioned on a lower portion having a predetermined separation distance from the flat cradle and includes a plurality of through holes into which the resistance measuring probe is insertable;
a coupling unit configured to allow the flat cradle, the upper plate and the lower plate to be coupled to each other; and
a pair of resistance measuring probes configured to obtain data for determining the resistance value by contacting the welded portion,
wherein the coupling unit includes a coupling bar and a coupling screw,
wherein the flat cradle, the upper plate and the lower plate each has coupling holes at 4 edge portions, and
wherein the upper plate, the flat cradle and the lower plate are coupled as the coupling bar sequentially passes through coupling holes disposed on the upper plate, the flat cradle and the lower plate.

\* \* \* \* \*